United States Patent [19]

Marshall et al.

[11] Patent Number: 5,073,543
[45] Date of Patent: Dec. 17, 1991

[54] CONTROLLED RELEASE FORMULATIONS OF TROPHIC FACTORS IN GANGLIOSIDE-LIPSOME VEHICLE

[75] Inventors: Lucia G. I. Marshall, St. Charles; Kanaiyalal R. Patel; Dikla G. Roufa, both of St. Louis, all of Mo.

[73] Assignee: G. D. Searle & Co., Chicago, Ill.

[21] Appl. No.: 222,436

[22] Filed: Jul. 21, 1988

[51] Int. Cl.$^5$ .............................................. A61K 47/36
[52] U.S. Cl. ...................................... 514/21; 530/350; 530/839; 530/848; 530/854
[58] Field of Search ................. 514/21; 530/350, 839, 530/848, 854

[56] References Cited

U.S. PATENT DOCUMENTS

| | | | |
|---|---|---|---|
| 3,311,539 | 3/1967 | Eberts | 514/526 |
| 4,185,095 | 1/1980 | Young | 514/21 |
| 4,230,691 | 10/1980 | Young | 530/854 |
| 4,287,184 | 9/1981 | Young | 514/21 |
| 4,308,166 | 12/1981 | Marchetti et al. | 514/21 |
| 4,522,803 | 6/1985 | Lenk | 424/1.1 |
| 4,593,091 | 6/1986 | della Valle | 536/53 |
| 4,639,437 | 1/1987 | della Valle | 514/54 |
| 4,762,915 | 8/1988 | Kung | 530/405 |
| 4,923,696 | 5/1990 | Appel | 530/350 |
| 5,017,375 | 5/1991 | Appel et al. | 530/839 |

FOREIGN PATENT DOCUMENTS

| | | | |
|---|---|---|---|
| 843695 | 3/1976 | Belgium . | |
| 183572 | 6/1986 | European Pat. Off. . | |
| 195169 | 9/1986 | European Pat. Off. . | |
| 0258111 | 3/1988 | European Pat. Off. | 514/21 |
| 57-146710 | 9/1982 | Japan . | |
| 85/0020 | 8/1985 | PCT Int'l Appl. . | |

OTHER PUBLICATIONS

Rosenberg et al., Chem. Abstr., vol. 106, entry 162490u (1988).
Unsicker et al., Chem. Abstr., vol. 110. entry, 833p (1989).
Rosenberg et al., Jour. Neurochemistry, vol. 98. No. 3, pp. 865-875 (1987).
Unsicker et al., Expt'l Cell Res., vol. 178, pp. 377-389 (1988).
M. Schwartz et al., Proc. Natl. Acad. Sci. USA, 79, 6080-6083 (1982).
M. Naoi et al., Biochemistry International, 9, 267-272 (1984).
P. Ghosh et al., Biochimica et Biophysica Acta., 632 (4), 562-572 (1980).
M. M. Jonah et al., Biochimica et Biophysica Acta., 541, 321-333 (1978).
Y. Tsao et al., Biochem. Biophys. Acta., 900(1), 79-87 (1987).
F. Gimbale et al., Journal of Neuroscience Research, 12, 355-375 (1984).
R. W. Ledeen, J. Neurosci. Res., 12, 147-159 (1984).

Primary Examiner—Donald G. Daus
Attorney, Agent, or Firm—J. Timothy Keane; Paul D. Matukaitis; Cynthia S. Kovacevic

[57] ABSTRACT

A formulation is described for systemic delivery and controlled release of a trophic factor. The formulation comprises a glycolipid carrier component which delivers trophic factor, such as nerve growth factor, to a target organ. The glycolipid carrier protects the trophic factor from degradation by enzymes typically endogenous to the human body.

7 Claims, 9 Drawing Sheets

CONTROLLED RELEASE FORMULATIONS OF TROPHIC FACTORS IN GANGLIOSIDE-LIPSOME VEHICLE

FIELD OF THE INVENTION

This invention is in the field of drug delivery systems and relates to formulations for controlled release of drugs for systemic therapeutic purposes. Of particular interest are controlled release formulations containing a trophic factor entrapped by a ganglioside-liposome vehicle.

BACKGROUND OF THE INVENTION

Systemic delivery of trophic factors, such as Nerve Growth Factor (NGF), is difficult to accomplish inasmuch as the human body contains enzymes within the circulatory system which would rapidly degrade trophic factors. Biological investigations of delivery of trophic factors so far have been limited to injection of large amounts of NGF to laboratory animals in order to study the effects of NGF on treatment of nerve damage. Such injections typically require large amounts of NGF because of rapid degradation.

Delivery systems for introducing proteins and other compounds into animals are well known. Of increasing interest are lipid membrane vesicles, e.g., liposomes for use in drug delivery systems. For example, U.S. Pat. No. 4,522,803 and PCT Application No. U.S. Pat. No. 85/00220 describe liposome preparations in the form of multilamellar vesicles to entrap bioactive compounds, such as hormones, proteins, or glycoproteins, for delivery of the bioactive compound to a target tissue. A study of glycolipid-liposome formulations for delivery of enzymes to target organs showed that sugar residues of the glycolipid component can affect distribution of the enzyme within the target organ [M. Naoi et al, *Biochemistry International,* 9, 267–272 (1984)]. Japanese Patent Document No. 57-146,710 describes liposome-type microcapsules having membrane walls composed of various components, such as phospholipids, gangliosides, cerebrosides and sulfatides, which encapsulate enzymes for delivery across the blood brain barrier.

Modified liposomes of various types have been devised and investigated as delivery vehicles in biological systems. For example, liposome formulations having different types of glycosides grafted onto liposome surfaces have been investigated for effect on tissue distribution of $^{125}$I-gamma-globulin [P. Ghosh et al, *Biochimica et Biophysica Acta.,* 632(4), 562–572 (1980)]. Multilamellar liposomes have been prepared having a marker compound (ethylenediaminetetraacetic acid, EDTA) encapsulated within a shell wall membrane composed of various asialoglycolipids, gangliosides, sialic acid or brain phospholipids; inclusion of the sialoganglioside component in the liposome membrane was shown to decrease the uptake of liposome by liver tissue to permit increased amounts of encapsulated EDTA to reach other organs [M. M. Jonah et al, *Biochimica et Biophysica Acta.,* 541, 321–333 (1978)].

Investigations have been made into the interaction of gangliosides and membrane-forming lipid materials. For example, a bilayer membrane structure can be formed by complementary packing of cone-shaped phosphatidylethanolamine material and inverted cone-shaped ganglioside $GD_{1a}$ material; these bilayer structures have been mentioned as useful in regulating membrane fluidity by changing ganglioside concentrations within the membrane in order to study Sendai virus induced leakage of the liposome [Y. Tsao et a, *Biochem Biophys Acta,* 900(1), 79–87 (1987)]. Artificial planar bilayer membranes have been made which are composed of phospholipids and monosialoganglioside ($GM_1$) micelles containing the ionophore gramicidin D. Membrane conductance was found to increase after the addition of $GM_1$ micelles at various ionophore/ganglioside ratios [F. Gimbale et al, *Journal of Neuroscience Research,* 12, 355–375 (1984)].

It is known that certain ganglioside materials can exhibit pharmacological activity in biological systems. For example, Italian Patent No. 1,046,051 mentions use of mono-, di-, tri- and tetra-sialogangliosides for treatment of disorders in the central and peripheral nervous systems such as paralysis of oculomotor nerves neuralagia of the trigeminus, paralysis of the facial nerve (Bell's paralysis), acute polyradiculoneuritis (Guillain-Barré syndrome), radiculitis, traumatic lesions of peripheral nerves, lesions of peripheral nerves due to toxic substances, alcoholic and diabetic polyneuritis, obstetric paralysis, paralysing sciatics, touching motorneurons, lateral amyotrophic sclerosis, muscular myelopathic atrophy, progressive bulbar paralysis, chronic myasthenia (Lambert Eaton syndrome), muscular dystrophy, changes in nervous synaptic transmission at CNS and PNS level, secondary consciousness troubles, cranial traumatism, cerebrum vascular disorders, thromboses and embolisms.

In a publication of R. W. Ledeen [*J. Neurosci Res.,* 12, 147–159 (1984)], there is a study of the neuritogenic and neuronotrophic properties of gangliosides showing that neurite formation is promoted by exogenously administered gangliosides. Exogenous gangliosides have been found to alter the onset lag of NGF-induced neurite recruitment of PC12 cells in the presence of fetal calf serum [R Katoh-Semba et al, *Soc. Neurosci. Abst.,* 10(1), 37 (1984)]. In a study of ganglioside influence on neuronal sprouting, rabbit anti-GM antibodies were found to block NGF-induced dorsal root ganglia sprouting of chicken embryo, which by inference may indicate promotion of neurite formation by gangliosides [M. Schwartz et al, *Proc. Natl. Acad. Sci. USA,* 79, 6080–6083 (1982)]. U.S. Pat. No. 4,593,091 describes inner ester ganglioside derivatives characterized in having a lactonic ring formed from a carboxyl group of an N-acetyl-neuraminic acid or N-glycolylneuraminic acid bonded to a hydroxy group of a carbohydrate comprising an N-acetylgalactosamine or N-acetylglycosamine moiety and glucose or galactose moiety, such ganglioside inner esters being more useful than the parent gangliosides in stimulating nerve regeneration and healing damaged nerve tissue. European Patent Application No. 183,572 describes mixtures of gangliosides (Svennerholm structure types $GM_1$, $GD_{1a}$, $GD_{1b}$, $GT_{ib}$) extracted from cattle cerebral cortex to have analgesic activity, particularly for treating peripheral neuropathy, trigeminus neuralgia and herpes Zoster. European Patent No. 195,169 describes administration of ganglioside $GM_1$ or its inner ester to increase cerebral blood flow without increase in arterial blood pressure for treatment of ischemia-induced cerebral stroke. U.S. Pat. No. 4,639,437 describes treatment of peripheral and central nervous disorders due to nerve damage by injury or disease with systemic administration of inner ester ganglioside derivatives in nebulized liquid or powder form by inhalation through respiratory membranes

SUMMARY OF THE INVENTION

Formulations for systemic administration or delivery of trophic factors such as Nerve Growth Factor (NGF) are provided by a combination comprising a trophic factor and a ganglioside-containing liposome incorporating the trophic factor. Such combination is provided by a composition comprising:
  (a) a therapeutically effective amount of a trophic factor for treating neurodegenerative diseases or for regenerating neuronal tissue or for protecting neural tissue from damage, such as may be induced by chemical, metabolic, mechanical or viral agents or by radiation; and
  (b) a carrier comprising a lipid component and a ganglioside component, said carrier associated with or containing the trophic factor to provide a delivery vehicle capable of slowly releasing the trophic factor and/or protecting the trophic factor from degradative enzymes.

These formulations are further characterized by the carrier being in the form of a vesicle or a liposome which contains the trophic factor. The liposome is further characterized by a wall or shell membrane comprising, or formed by, the lipid component and the ganglioside component. The shell wall membrane of this ganglioside-containing liposome will likely also contain a stabilizing component such as a steroid compound or its derivative.

BRIEF DESCRIPTION OF THE DRAWINGS

The drawings (not to scale) illustrate various embodiments of the invention, as follows.

DESCRIPTION OF PREFERRED EMBODIMENTS

Successful drug delivery formulations must satisfy four criteria: (1) capability to form a stable membrane wall to encapsulate a drug to be delivered; (2) capability to form vesicles of a size large enough to minimize decomposition by hepatocytes in the liver and small enough to minimize decomposition by Kupffer cells of the liver; (3) capability to protect trophic factor from rapid enzymatic degradation; and (4) capability to release the active drug at the target tissue at a therapeutically-effective rate. Ganglioside-containing liposome vesicles have now been found to satisfy all four criteria for systemic delivery of trophic factors. A further benefit provided by the formulations of the invention is the simultaneous delivery to a target organ of both trophic factor, e.g., NGF or NGF-like material, and ganglioside, which in combination provide an enhanced therapeutic benefit Trophic factors mediate interactions between cells. These interactions are restricted in roughly the same way as hormones and neurotransmitters are restricted. Trophic molecules, hormones and neurotransmitters are extracellular messengers that are distinguished primarily by the strategy of their action. Trophic factors are molecules required for cellular survival, growth, and/or differentiation. Neurotrophic factors mediate interactions affecting neuronal tissue. Unlike conventional synaptic events between nerve cells that are measured on the time scale of milliseconds or seconds, neurotrophic interactions transpire over days, months or even the lifetime of the organism. The prototype of a neurotrophic factor is NGF. The term "NGF-like material" embraces molecules which are characterized in having the capability to stimulate or potentiate survival, growth and/or differentiation of neuronal tissue. This term embraces the prototype trophic factor, NGF, as well as β-NGF and substantially biologicallyequivalent analogues of NGF and β-NGF, such as des 1–9 NGF.

NGF and NGF-like proteins are protected from enzymatic degradation within the mammalian system when encapsulated within a glycolipid carrier characterized in having a ganglioside component. These ganglioside-containing glycolipid carriers entrap the trophic factor to provide a system, typically a ganglioside-modified liposome vehicle, which protects the NGF-like protein from degradation by enzymes of the human body.

Figure 1:
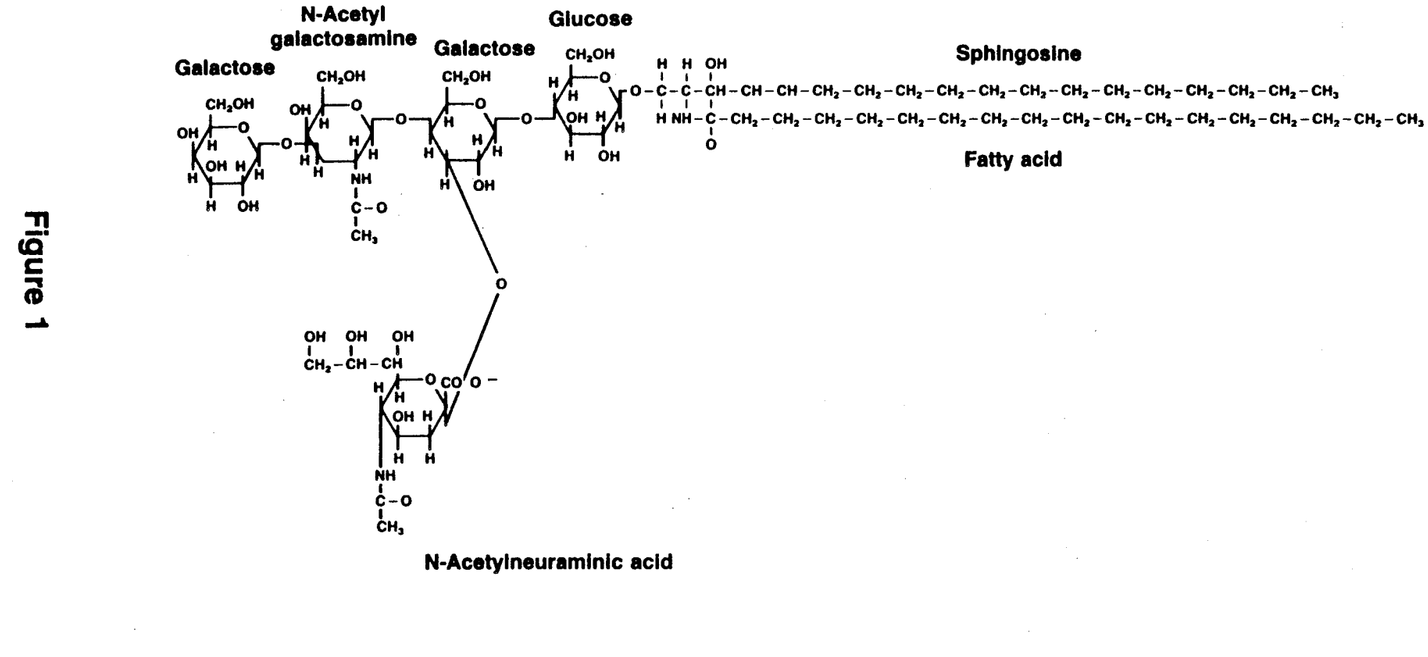
FIG. 1 is a structural formula for a ganglioside typically useful as a component in a glycolipid carrier.

Ganglioside-modified liposome vehicles have now been found as particularly suitable for systemic delivery of trophic factors. The terms "ganglioside-modified liposome vehicle" or "ganglioside-containing liposome vehicle" describe a globular-shaped entity composed of a wall membrane having one or more layers which contain about 5% to about 20% ganglioside component inserted within a lipid component. The term "ganglioside" describes a family of naturally occurring acidic glycosphingolipids containing a hydrophilic oligosaccharide moiety with one or more neuraminic acids groups and any derivatives thereof. Included in such ganglioside derivatives are natural gangliosides which have been chemically modified, for example, by formation of internal esters, amides, acylated derivatives, salts and the like. Gangliosides are found in membranes of almost all tissues, with high concentration occurring in neural tissues especially brain cortical tissue. Mammalian brains contain gangliosides typically composed of four basic structural units: a long-chain aminoalcohol, a fatty acid, an oligosaccharide moiety and one or more sialosyl residues, as depicted in FIG. 1.

The long-chain aminoalcohol is present in brain gangliosides and is identified as 4-sphingosine and its longer-chain analog as 4-eicososphingenine. These compounds are commonly called sphingosines. Corresponding saturated compounds are also present in gangliosides in minor proportions.

The fatty acid is linked by means of an amide bond to the sphingosine base. In brain gangliosides, this fatty acid is more than 95% accounted for by stearic acid. Other fatty acids present in minor proportions include arachidonic acid, palmitic acid or palmitoleic acid. The aminoalcohol plus the fatty acid form a unit called "ceramide", which represents the hydrophobic part of the ganglioside molecule.

The oligosaccharide chain linked to ceramide characterizes the large family- of glycosphingolipids to which gangliosides belong. The sphingolipids are classified in two subgroups, based on the carbohydrate immediately linked to ceramide. The first and smaller subgroup is derived from galactosylceramide. Most of the glycosphingolipids and all gangliosides belong to the subgroup derived from glucosylceramide.

Sialic acid is present in brain gangliosides mainly in the N-acetyl form, but in some ganglioside species the N-glycolyl form has been identified. This residue is generally termed neuraminic acid (NANA or NGNA).

The hydrophilicity of gangliosides is due to the oligosaccharide chain and to the number of sialosyl residues linked to this chain.

Figure 2:
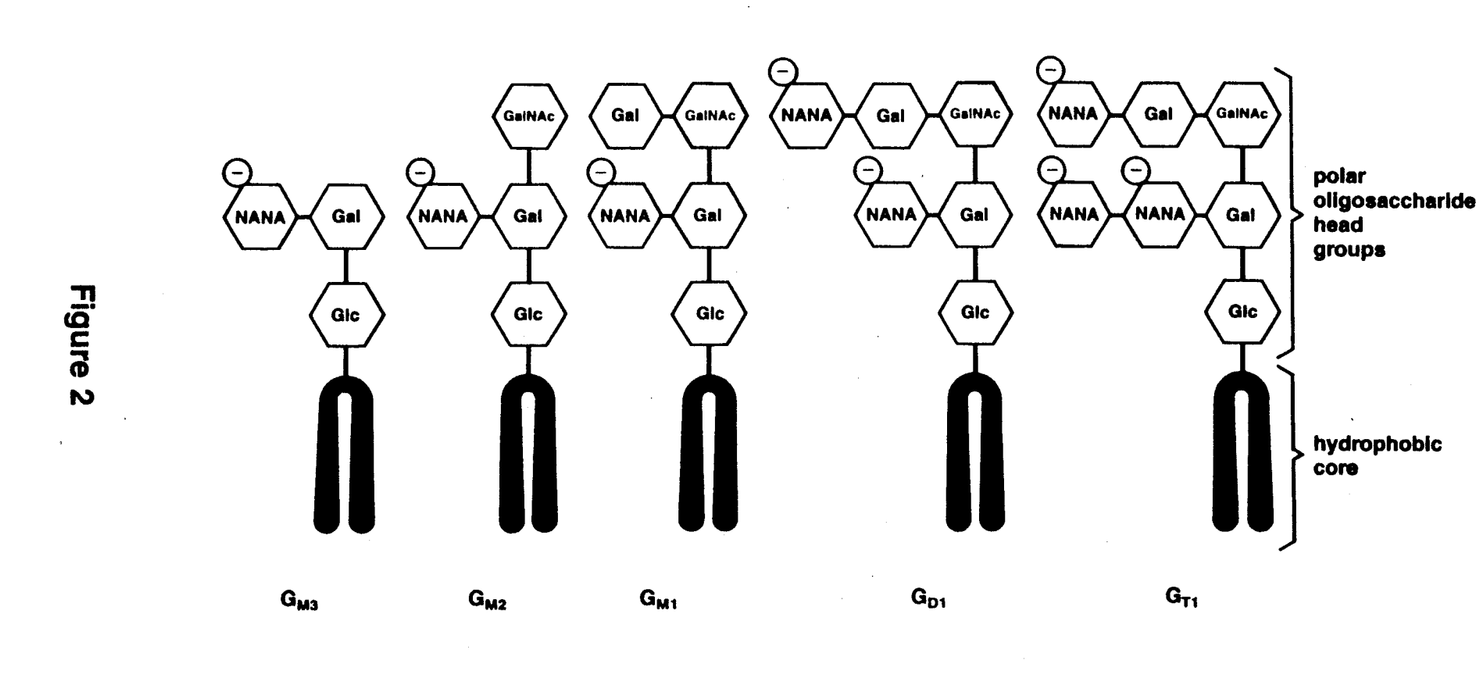
FIG. 2 is a block diagram of several representative gangliosides labelled with standard designations.

The five main mammalian brain gangliosides which comprise 90% of the total ganglioside content of mammalian brain are shown in block diagram form in FIG. 2. These five gangliosides are shown with their standard designations in accordance with the Svennerholm nomenclature which directs that substituents on the root oligosaccharide are given at the beginning of the name by a Roman numeral that indicates the monosaccharide residue (counting from ceramide) on which the substituent is located. A subscript arabic numeral indicates the position of the glycosidic linkage, $GM_1$, $GM_2$, $GM_3$, $GD_1$ and $GT_1$. The letters M, D, and T refer to the number of sialic acid residues (mono, di, and tri, respectively). The number that follows the letter is determined by substracting the number of uncharged sugar residues from 5; thus NANA=N-acetylneuraminic (sialic) acid; Gal=galactose; Glc=glucose; GalNAc=N-acetyl-galactosamine. Gal, Glc, and GalNAc are all uncharged; NANA carries a negative charge.

Figure 3:
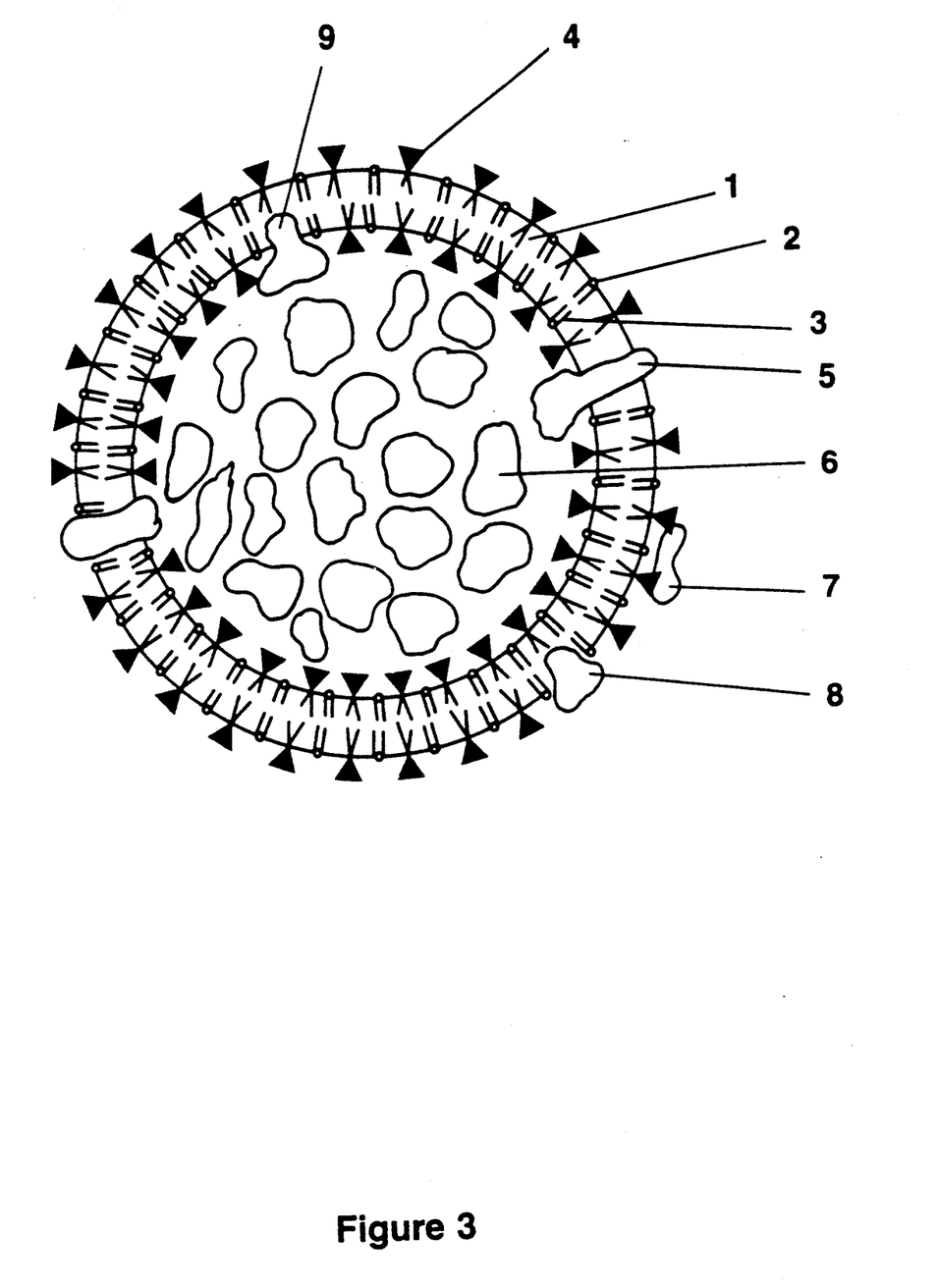
FIG. 3 shows liposome components 1 through 4 which include unilamellar lipid bilayer and gangliosides 4. Localization possibilities of trophic molecules associated with or contained within the liposome are shown as elements 5 through 9.
Figure 4:
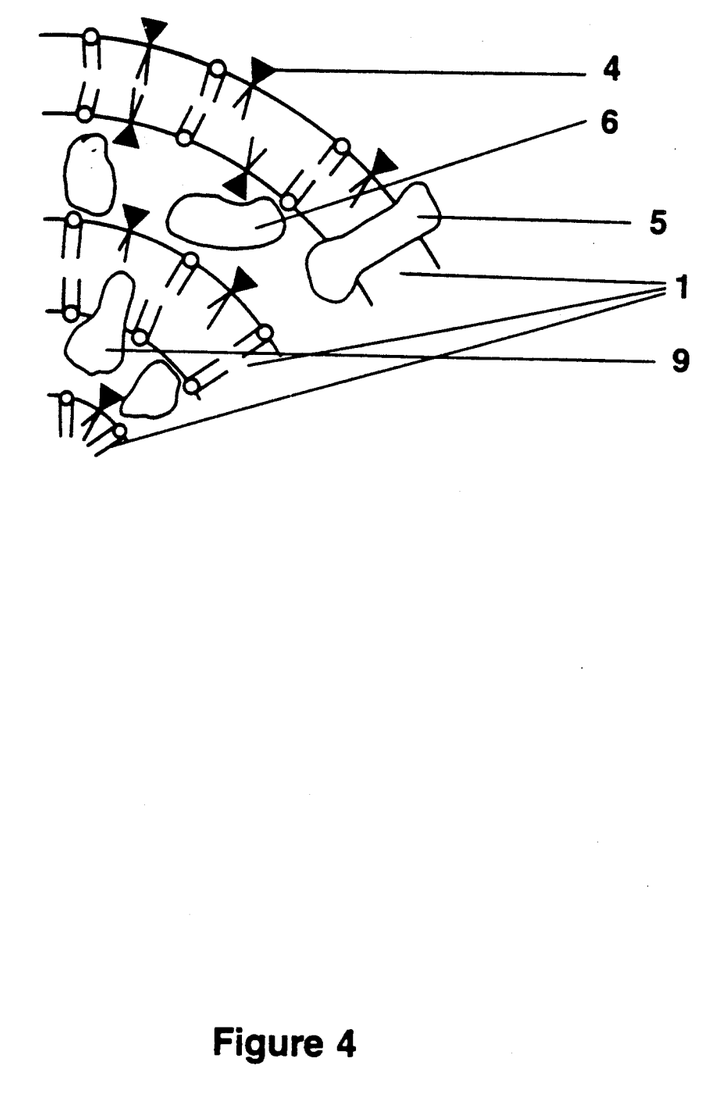
FIG. 4 shows liposome components 1 and 4 which include multilamellar lipid bilayer 1 and gangliosides 4. Trophic molecule localization possibilities within the liposome are shown as elements 5, 6 and 9.

Liposomes are vesicles having a shell wall composed of bilayer membranes surrounding an entrapped aqueous phase. Liposome vesicles may have a single membrane bilayer or may be in the form of an onion-skin-like structure wherein adjacent concentric membrane bilayers are separated by a water layer. Liposomes typically may be prepared by suspending a phospholipid in an organic solvent in a reaction vessel, evaporating this mixture to dryness to form a phospholipid residue or film on the inner wall of the reaction vessel, then adding water to swell the phospholipid film, and then mechanically agitating the film to form vesicles having a shell wall bilayer membrane. This bilayer membrane is characterized in having the polar, hydrophilic head of the lipid component directed toward the aqueous phase, while the non-polar, hydrophobic tails of the lipid component is directed toward the inside of the bilayer membrane As illustrated in FIG. 3, the drug delivery system comprises a vesicle which has a membrane wall, termed membrane bilayer 1, containing phospholipids with polar hydrophillic head groups 2 and with non-polar hydrocarbon tails 3. Interspersed among the phospholipids are gangliosides which have polar and non-polar aspects structurally similar to, and oriented like, the phopholipids. When so oriented the phospholipid and ganglioside head groups and tails form the membrane walls. As illustrated in FIG. 4, the drug delivery system may also comprise a vesicle which has two or more lipid bilayers 1 which form a multilamellar liposome. Trophic factor is associated with or entrapped within the vesicle as indicated in FIGS. 3 and 4 at positions 6, 7, 8 and 9 relative to the vesicle walls 1.

Liposomes are formed by adding an aqueous solution to lipid films and agitating. The polar head groups 2 of the lipids orient themselves to the aqueous environment, whereas the non-polar or hydrophobic tails 3 align themselves adjacent to other hydrophobic lipids or moieties.

Lipids used to make the liposome membranes are typically phospholipids, cholesterol, modified cholesterol compounds such as cholesteryl-3-polyoxyethylenes ("chol-1") [see K. R. Patel et al, *Biochem-Biophys. Acta*, 797, 20–26 (1984)]. The lipid typically is mixed together with ganglioside to form a ganglioside-containing lipid film. Then trophic factor, e.g., NGF or NGF-like protein in a buffer solution, is added to the ganglioside-containing lipid film to form vesicles containing the trophic factor.

Ganglioside-containing liposome membranes are made during the preparation of the lipid film. Gangliosides material in an amount from about 5 to about 20% by weight is added to the stock lipid solution prior to rotary evaporating the lipids to form the lipid film. Typically useful gangliosides are $GM_1$, $GD_1$ and $GT_1$. Gangliosides 4 orient themselves in the membrane bilayer with the polar head group in the aqueous environment and the hydrophobic tails aligning themselves in the non-polar hydrocarbon environment.

Trophic factor is introduced during the formation of the liposome by adding a solution of approximately 1 mg/ml trophic factor (dissolved in the buffer) to the lipid film. Once the trophic factor is added to the lipid film and agitated, the lipids form the membrane walls entrapping trophic factor at 7, 8 and 9, intercalating at 5, or encapsulating at 6 the trophic factor that is available.

Ganglioside-modified liposome vehicles were prepared in accordance with the following detailed procedures. Preparation of these vehicles involves bringing together one or more lipid materials and one or more glycolipid materials. Suitable lipid materials for making these vehicles include phospholipid materials and cholesterol derivatives. Examples of phospholipids are dipalmitoyl phosphatidylcholine (DPPC) also known as "lecithin", distearoyl phosphatidylcholine (DSPC), dimyristyl phosphatidylcholine (DMPC), dipalmitoyl phosphatidylethanolamine (DPPE), distearoyl phosphatidylethanolamine (DSPE), dimyristyl phosphatidylethanolamine (DMPE), phosphatidylethanolamine (PE), phosphatidylserine (PS), dipalmitoyl phosphatidylserine (DPPS), distearyol phosphatidylserine (DSPS), dimyristoyl phosphatidylserine (DMPS). Suitable cholesterol derivatives for use in making lipids include cholesterol-1 (triethoxycholesterol or cholesteryl-3-polyoxyethylene CHOL-1). Suitable glycolipid materials are mixed brain-bovine gangliosides typically those gangliosides identified as $GM_1$, $GD_{1a}$, and $GT_1$, the formulae of which are as follows:

$GM_1$ $II^3\alpha$-NeuAc-GgOse$_4$Cer
$GD_{1a}$ $II^3\alpha$-NeuAc-$IV^3$-$\alpha$-NeuAc-GgOse$_4$Cer
$GD_{1b}$ $II^3\alpha$-(NeuAo)$_2$GgOse$_4$Cer
$GT_{1b}$ $II^3\alpha$-(NeuAc)$_2$-$IV^3$-NeuAc-GgOse$_4$Cer Lipids and gangliosides were dissolved in organic solvents. Then, lipid-ganglioside films were prepared by evaporation of the organic solvents at 45° C. to form smooth lipid films.

The NGF, or $^{125}$I-NGF, was dissolved in a phosphate-buffered saline (PBS) which was then added to the dried lipid films. The NGF was encapsulated in liposomes by stirring lipid film with an aqueous solution of NGF. Multiple washing and centrifugation steps at 5000 rpm for 20 minutes were performed to separate the liposome encapsulated NGF (pellet) from unencapsulated NGF. Formulations prepared in accordance with these procedures are shown in Table 1.

TABLE I

Formulations and Percent $^{125}$-I-NGF Encapsulation by Vesicles

| Formulation | | | % $^{125}$I-NGF Encapsulation* |
|---|---|---|---|
| A | 50.00 mg | Chol-1 | 20% |
|   | 5.00 mg | Gangliosides | |
| B | 60.00 mg | Chol-1 | 22% |
|   | 5.00 mg | Gangliosides | |
| C | 80.00 mg | Chol-1 | 37% |
|   | 20.00 mg | Gangliosides | |
| D | 39.60 mg | DPPC | 31% |
|   | 10.40 mg | Cholesterol | |
|   | 12.50 mg | Gangliosides | |
| E | 50.00 mg | Chol-1 | 26% |
|   | 12.50 mg | Gangliosides | |
| F | 50.00 mg | Chol-1 | 23% |
|   | 12.50 mg | $G_{M1}$ | |
| G | 50.00 mg | Chol-1 | 15% |
|   | 12.50 mg | $G_{D1a}$ | |
| H | 50.00 mg | Chol-1 | 17% |
|   | 12.50 mg | $G_{T1}$ | |
| I | 31.84 | DPPC | 17% |
|   | 8.36 mg | Cholesterol | |
|   | 19.80 mg | $G_{M1}$ | |

*% Encapsulation = $\frac{\text{CPM } ^{125}\text{I-NGF in final pellet}}{\text{CMP } ^{125}\text{I-NGF in starting material}} \times 100$ Particle size determinations were made on various formulations with and without NGF encapsulation. Particle size uniformity determinations were made by light scattering techniques. All liposome formulations were filtered through 1.2 micron cellulose filter before the light scattering measurements. Table II shows side-by-side comparisons of the various formulations with and without encapsulated NGF.

TABLE II

| Liposome Formulation | Particle Diameter Range (microns ± SD) | |
|---|---|---|
| | Smaller Diameter | Larger Diameter |
| Chol-1 | 0.63 ± 0.48 | 2.18 ± 0.71 |
| Chol-1:5% Gangl | 0.75 ± 0.55 | 2.18 ± 0.71 |
| Chol-1:20% Gangl | 0.70 ± 0.62 | 3.11 ± 1.06 |
| Chol-1:5% Gangl:NGF | 0.74 ± 0.40 | 2.05 ± 0.73 |
| DSPC:Chol:PS | 0.75 ± 0.51 | 1.80 ± 0.63 |
| DSPC:Chol:PS:5% Gangl | 0.68 ± 0.49 | 2.10 ± 0.72 |
| DSPC:Chol:PS:20% Gangl | 0.77 ± 0.54 | 1.93 ± 0.67 |
| DSPC:Chol:PS:5% Gangl:NGF | 0.80 ± 0.56 | 2.41 ± 0.81 |
| DPPC:Chol | — | 3.18 ± 0.82 |
| DPPC:Chol:5% Gangl | — | 3.94 ± 1.06 |
| DPPC:Chol:20% Gangl | 1.06 ± 0.61 | 4.29 ± 1.14 |
| DPPC:Chol:5% Gangl:NGF | — | 1.27 ± 0.30 |

A useful formulation will comprise a range of particle sizes for the ganglioside-modified liposome is from about $0.01\mu$ to about $10\mu$. A preferred range of particle sizes is from about $0.01\mu$ to about $5\mu$, and a more preferred range is form $0.01\mu$ to about $2\mu$. It is most preferred that a therapeutic dose of the NGF-containing formulation be comprised of particles of which at least 75 percent have mean particle diameters between about $0.01\mu$ and $2\mu$. As shown by the data in Table II, the tested liposome preparations typically showed bimodal distribution based on mean particle size diameters as determined by light-scattering techniques. Vesicle size distribution may be varied by use of many known techniques such as sonification and microfluidization techniques.

Biological Evaluation

The formulations of the invention were evaluated by establishing the tissue distribution and bioavailability of the prototypic neurotrophic factor NGF following systemic administration of unencapsulated NGF and in combination with various drug delivery formulations or carriers.

The NGF used in the studies for encapsulation was 2.5S subunit of NGF purified from adult male mouse submaxillary glands according to the method of Bocchini and Angeletti, Proc. Natl. Acad. Sci. (USA), 4, 787–794 (1969). The iodination of 2.5S NGF used in the tissue distribution studies was accomplished using the lactoperoxidase method [Marchalonis, Biochem. J., 113, 299–305 (1969)]. Ten $\mu$g of 2.5S NGF was reacted with 1 mCi of Na$^{125}$I (Amersham). The amount of $^{125}$I incorporated into the protein as determined by number of counts, ranged from 70–90% of available $^{125}$I which corresponded to specific activity of 1.8–2.3 Ci/$\mu$mole NGF. The labeled protein was separated from unincorporated $^{125}$I by chromatography on Sephadex G-25 M PD-10 Columns (Pharmacia).

Radiolabeled $^{125}$Iodine-nerve growth factor ($^{125}$I-NGF) was encapsulated by various liposome formulations. The materials used in the biological studies illustrated herein were as follows: $^{125}$I-NGF without carrier ("A"); $^{125}$I-NGF encapsulated by DPPC:cholesterol (2:1 molar ratio) containing 5% mixed gangliosides (Sigma Formulation "B"); or $^{125}$I-NGF encapsulated by cholesterol-1 (triethoxycholesterol) containing 5% mixed gangliosides (Formulation "C"). The various formulations were injected into the tail vein (I.V.) of 2 to 3 months-old Swiss-Webster mice of approximately 30g body weight. Each animal was injected with a maximum of 2$\mu$Ci of radiolabeled ligand in a total volume of 0.20 ml. At given time intervals following I.V.

administration of the test formulation, the mice were anesthesized with 0.05-0.10 ml Nembutal (Abbott Laboratories) by intraperitoneal injections. The animals were weighed and the following tissues were removed: blood, liver, spleen, kidney, lungs, intestine, tibia (bone marrow), muscle, trachea and brain. Each tissue was weighed and the amount of radioactive label present was measured. The radioactivity of each organ and tissue weight obtained from each time point were expressed as follows:

$$\% \text{ Injected Dose } (\% \text{ I.D.}) = \frac{CPM \text{ organ}}{CPM \text{ Injected Dose}} \times 100$$

Table II reports percent injected dose (% I.D.) in various body organs. The total uptake of liposomes in certain organs was estimated in accordance with published procedures. The amount of vesicles present in the blood was calculated assuming that blood comprised 7.3% of the total body weight [M. R. Mauk et al, *Proc. Natl. Acad. Sci USA*, 77, 4430-4434 (1980)].

Total blood (CPM) =

$$\frac{CPM \text{ in blood sample} \times (0.073 \times \text{body weight})}{\text{blood sample weight}}$$

Total muscle is 14% of total body weight for mice [ICRP Reference Manual 1975, W. F. Snyder, Oxford, Pergamon Press, p.284].

Total muscle (CPM) =

$$\frac{CPM \text{ in muscle sample} \times (0.14 \times \text{body weight})}{\text{muscle sample weight}}$$

For bone marrow determination, both tibia from each mouse were counted and this value was multiplied by 44 [M. W. Rosenthal et al, *Health Phys.*, 22, 743-748 (1977)].

Total bone marrow (CPM) = [CPM in pair of tibia] × 44

Table III shows results of distribution of $^{125}$I-NGF in various tissues following I.V. administration of formulations A, B or C into mice and sampling at intervals of 1, 24 and 96 hours after injection.

TABLE III

Comparison of Vesicles:
NGF Without Carrier vs. NGF DPPC:Chol:Gangliosides vs. NGF Chol-1:Gangliosides

| Organ | | % I.D. I.V. Administration | | |
|---|---|---|---|---|
| | | 1 Hour | 24 Hours | 96 Hours |
| Liver | A | 10.79 ± 0.57* | 0.91 ± 0.06 | 0.50 ± 0.04 |
| | B | 51.18 ± 1.40 | 18.82 ± 2.19 | 2.37 ± 0.07 |
| | C | 52.08 ± 3.14 | 27.17 ± 1.78 | 6.54 ± 0.88 |
| Bone Marrow | A | 10.23 ± 2.05 | 0.54 ± 0.09 | 0.39 ± 0.03 |
| | B | 16.52 ± 6.07 | 5.61 ± 1.09 | 1.77 ± 0.38 |
| | C | 13.77 ± 4.41 | 6.08 ± 2.63 | 1.50 ± 0.59 |
| Spleen | A | 0.81 ± 0.17 | 0.05 ± 0.01 | 0.02 ± 0.00 |
| | B | 9.49 ± 0.82 | 3.33 ± 1.28 | 0.62 ± 0.11 |
| | C | 9.14 ± 1.40 | 3.32 ± 1.32 | 1.08 ± 0.32 |
| Blood | A | 8.69 ± 1.12 | 0.21 ± 0.02 | 0.07 ± 0.02 |
| | B | 6.08 ± 1.97 | 0.37 ± 0.11 | 0.11 ± 0.03 |
| | C | 3.00 ± 0.35 | 0.22 ± 0.03 | 0.15 ± 0.04 |
| Lungs | A | 1.08 ± 0.22 | 0.15 ± 0.09 | 0.05 ± 0.01 |
| | B | 4.66 ± 1.07 | 0.76 ± 0.13 | 0.21 ± 0.04 |
| | C | 5.24 ± 0.40 | 1.42 ± 0.36 | 0.48 ± 0.01 |
| Intestine | A | 5.92 ± 0.78 | 0.19 ± 0.03 | 0.10 ± 0.04 |
| | B | 2.53 ± 0.21 | 0.52 ± 0.09 | 0.15 ± 0.02 |
| | C | 1.94 ± 0.09 | 0.36 ± 0.07 | 0.22 ± 0.05 |

TABLE III-continued

Comparison of Vesicles:
NGF Without Carrier vs. NGF DPPC:Chol:Gangliosides vs. NGF Chol-1:Gangliosides

| Organ | | % I.D. I.V. Administration | | |
|---|---|---|---|---|
| | | 1 Hour | 24 Hours | 96 Hours |
| Muscle | A | 3.85 ± 0.61 | 0.09 ± 0.00 | 0.05 ± 0.02 |
| | B | 2.10 ± 0.34 | 0.40 ± 0.11 | 0.15 ± 0.05 |
| | C | 1.54 ± 0.23 | 0.35 ± 0.06 | 0.17 ± 0.02 |
| Kidney | A | 3.37 ± 0.31 | 0.33 ± 0.03 | 0.14 ± 0.01 |
| | B | 1.51 ± 0.13 | 0.20 ± 0.03 | 0.07 ± 0.01 |
| | C | 1.12 ± 0.17 | 0.21 ± 0.04 | 0.11 ± 0.02 |
| Trachea | A | 4.47 ± 0.61 | 6.07 ± 1.34 | 5.31 ± 2.05 |
| | B | 0.85 ± 0.10 | 7.17 ± 1.79 | 8.54 ± 1.61 |
| | C | 1.18 ± 0.28 | 6.51 ± 1.68 | 8.82 ± 2.26 |
| Brain | A | 0.16 ± 0.03 | 0.00 ± 0.00 | 0.00 ± 0.00 |
| | B | 0.15 ± 0.02 | 0.04 ± 0.01 | 0.01 ± 0.00 |
| | C | 0.10 ± 0.02 | 0.03 ± 0.01 | 0.02 ± 0.00 |
| % Recovered | A | 49.36 ± 3.94 | 8.55 ± 1.26 | 6.55 ± 1.82 |
| | B | 95.08 ± 4.61 | 37.23 ± 2.15 | 14.02 ± 1.03 |
| | C | 89.11 ± 2.79 | 45.68 ± 2.66 | 19.10 ± 2.10 |

A = NGF without carrier
B = NGF DPPC:Chol:Gangliosides
C = NGF Chol-1:Gangliosides
*Each value represents an average of four replicates ± standard deviation.

Figure 5:
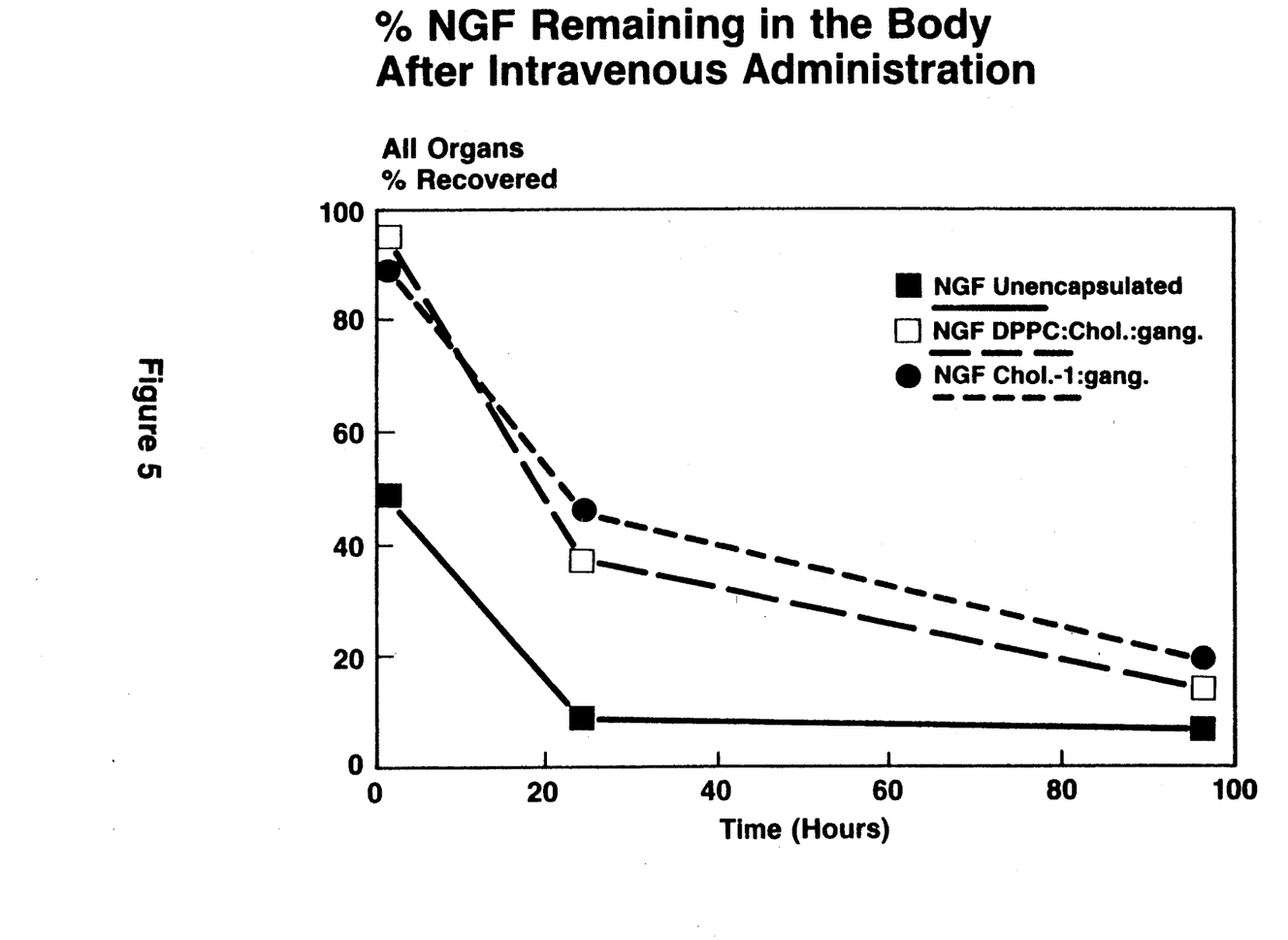
FIG. 5 is a graph showing the effect of NGF encapsulation on the percent injected dose of $^{125}$I-NGF remaining in major organs following intravenous administration of $^{125}$I-NGF unencapsulated (■); encapsulated by DPPC:cholesterol:gangliosides (□); or cholesterol-1:gangliosides (●).

The amount of $^{125}$I-NGF present within major organs of the body was greater when $^{125}$I-NGF was encapsulated by formulation B or C compared to unencapsulated $^{125}$I-NGF A. The enhanced bioavailability persisted for at least 96 hours after injection. The increase in encapsulated $^{125}$I-NGF recovered from all measured organs was approximately 2 fold at 1 hour, 5 fold at 24 hours and 3 fold at 96 hours following I.V. administration (FIG. 5).

Figure 6:
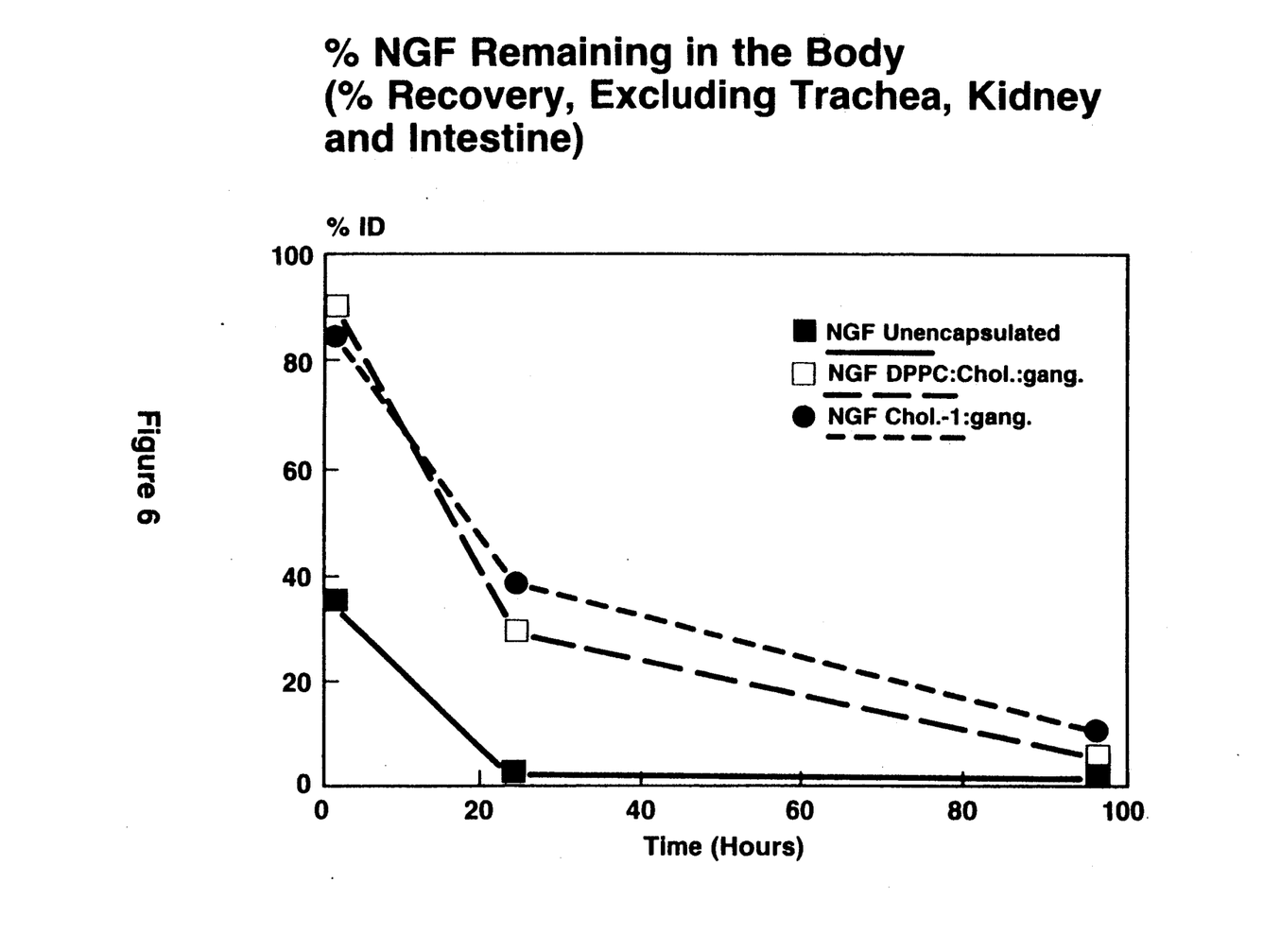
FIG. 6 is a graph demonstrating the effect of NGF encapsulation on the percent injected dose of $^{125}$I-NGF remaining in all major organs except trachea, kidney and intestine at various time points following intravenous administration of $^{125}$I-NGF unencapsulated ( ); encapsulated by DPPC:cholesterol: gangliosides (□); or cholesterol-1:gangliosides (●).

Organs involved in the degradation and/or elimination of proteins and $^{125}$I-NGF are the intestine, kidney and trachea. As shown in FIG. 6, when these organs were not included in calculating percent recovery of $^{125}$I-NGF, formulations B and C showed approximately a 7-fold increase in bioavailability of $^{125}$I-NGF over unencapsulated $^{125}$I-NGF at the 24-hour interval after injection. Both formulation B and C provided enhanced bioavailability of $^{125}$I-NGF. All unencapsulated $^{125}$I-NGF was degraded and eliminated within 24 hours of administration (FIG. 6).

Figure 7:
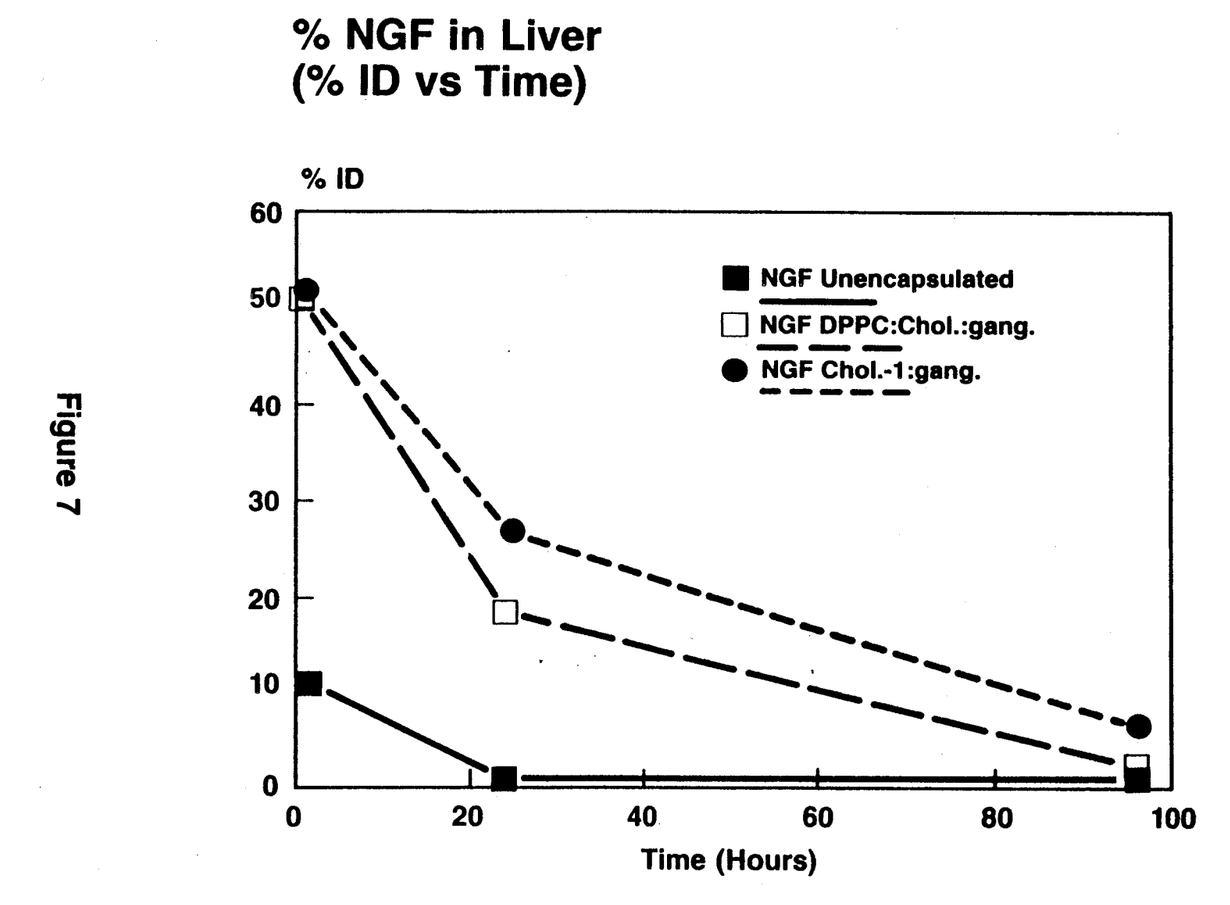
FIG. 7 is a graph illustrating the effect of NGF encapsulation on the percent injected dose of $^{125}$I-NGF present in the liver at various time intervals following intravenous administration of $^{125}$I-NGF unencapsulated ( ); encapsulated by DPPC:cholesterol: gangliosides (□); or cholesterol-1:gangliosides (●).
Figure 8:
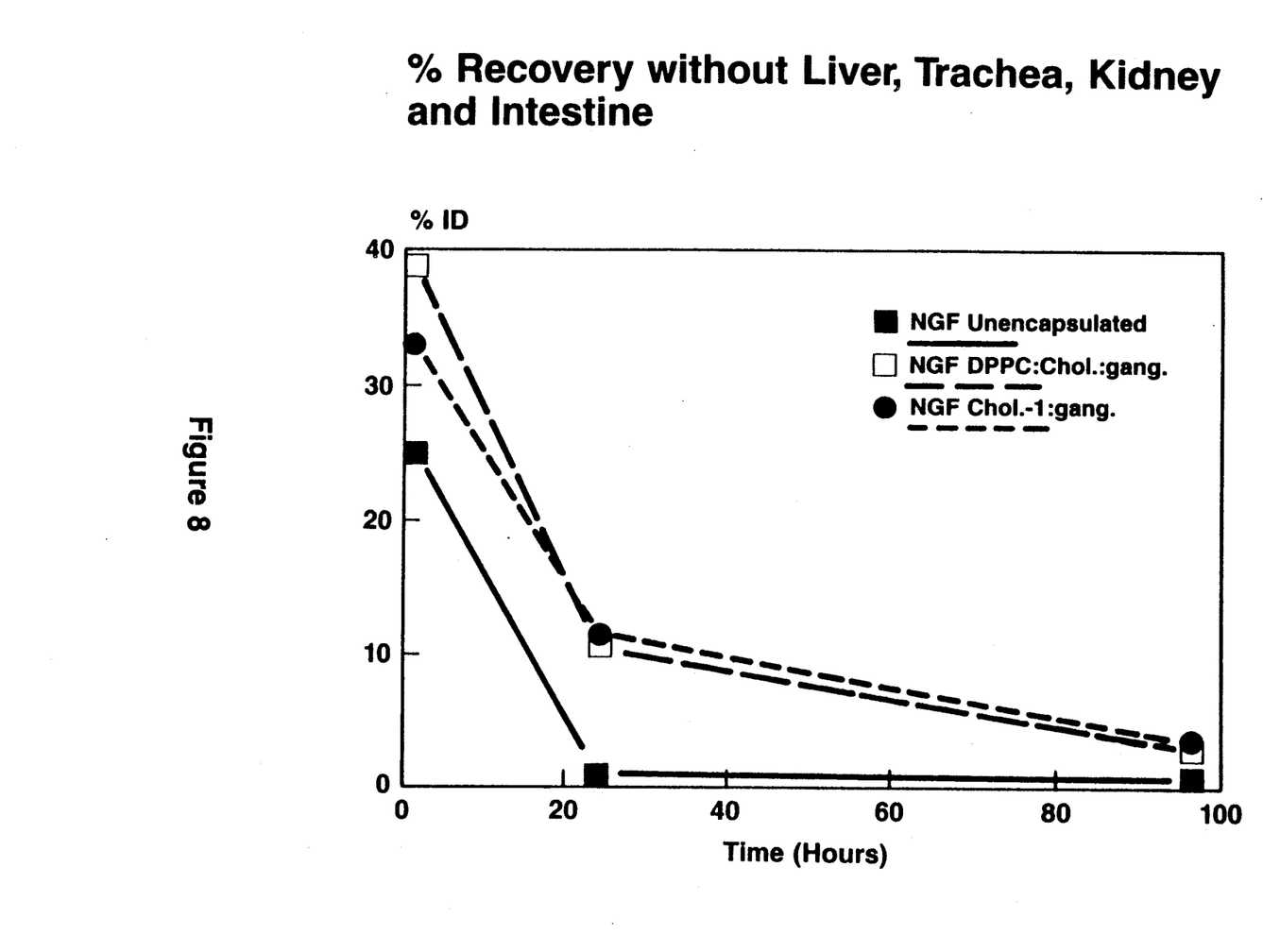
FIG. 8 is a graph demonstrating the effect of NGF encapsulation on the percent injected dose of $^{125}$I-NGF present in all major organs excluding the liver, trachea, kidney and intestine at various time points following intravenous administration of $^{125}$I-NGF unencapsulated (■): encapsulated by DPPC:cholesterol-gangliosides (□); or cholesterol-1: gangliosides (●).

As shown in FIG. 7, % I.D of $^{125}$I-NGF present in the liver 1 hour after I.V. administration reaches 50% for encapsulated $^{125}$I-NGF, compared to 10% when $^{125}$I-NGF is injected unencapsulated. The liver, however, did not sequester all available encapsulated $^{125}$I-NGF. One hour following injection 30 to 40% I.D. encapsulated $^{125}$I-NGF was within the circulatory system or taken up by other organs compared to 25% I.D. for unencapsulated $^{125}$I-NGF (FIG. 8). The amount of $^{125}$I-NGF present in all measured organs, excluding liver, trachea, kidney and intestine, was also significantly greater when measured at 24 and 96 hours following administration of encapsulated $^{125}$I-NGF compared to unencapsulated NGF (10% vs. 1% I.D. at 24 hours and 3% vs. 0.6% I.D. at 96 hours).

Figure 9:
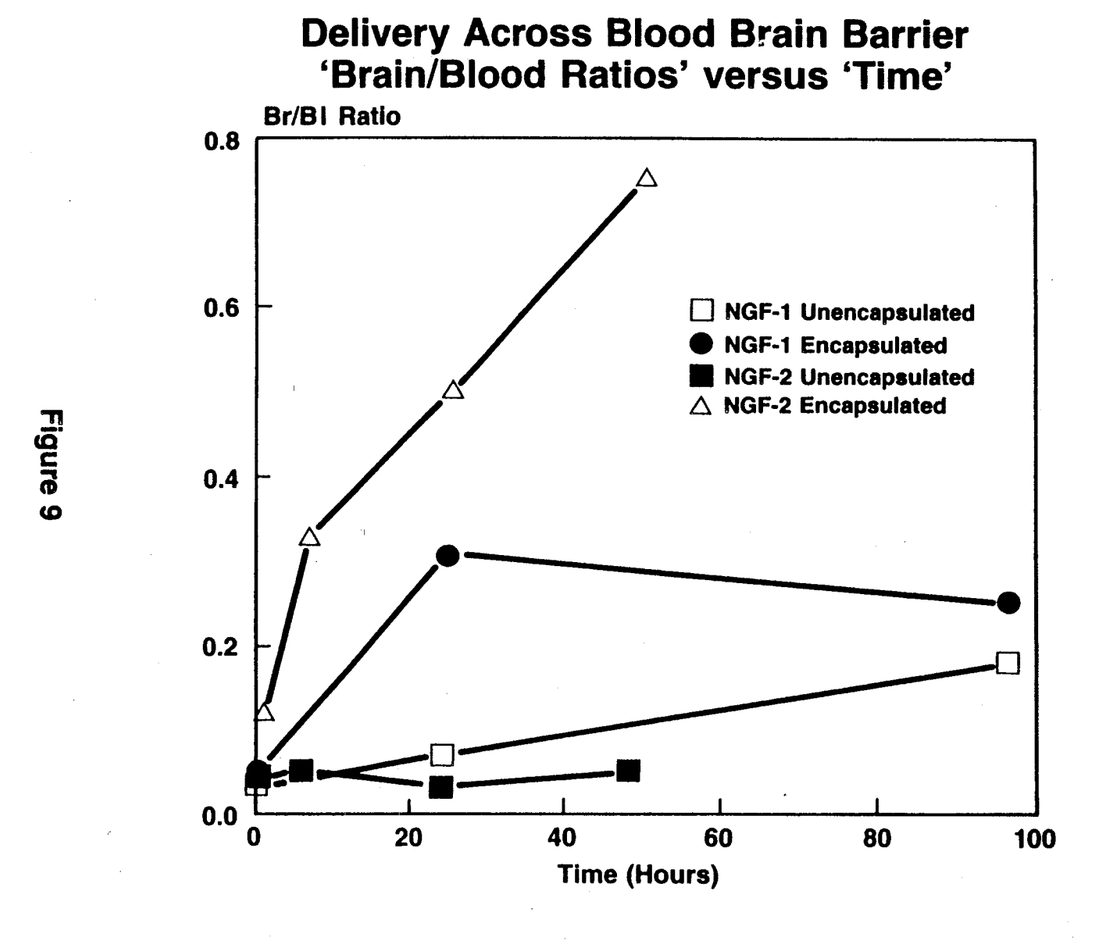
FIG 9 is a graph showing the effect of NGF encapsulation on $^{125}$I-NGF brain/blood ratio at various time points following intravenous administration of $^{125}$I-NGF unencapsulated (□); encapsulated by cholesterol-1:5% gangliosides (●); or cholesterol-1:20% gangliosides (Δ).

Delivery of $^{125}$I-NGF across the blood-brain barrier was estimated using the formula % I.D. Brain/% I.D. blood. The two liposome formulations used were 95% CHOL-1 with 5% ganglioside (NGF-1 encapsulated) and 80% CHOL-1 with 20% ganglioside (NGF-2 encapsulated). All encapsulated $^{125}$I-NGF formulations showed significantly higher brain/blood ratios compared to unencapsulated $^{125}$I-NGF.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method for administering systemically a therapeutically-effective amount of a trophic factor to a mammal for treatment of a neurodegenerative disease, said method comprising administering a formulation comprised of:
   (a) a therapeutically effective amount of a trophic factor selected from NGF, β-NGF and des 1-9 NGF, for treating a neurodegenerative disease or for regenerating neuronal tissue or for protecting neural tissue from damage induced by chemical, metabolic, mechanical or viral agents or by radiation; and
   (b) a carrier comprising a phospholipid component and a ganglioside component selected from $GM_1$, $GD_1$ and $GT_1$ ganglioside types, said carrier containing said trophic factor;
   whereby a formulation is provided capable of slowly releasing the trophic factor or protecting the trophic factor from degradative enzymes.

2. The method of claim 1 further characterized by said carrier being in the form of a vesicle which contains the trophic factor.

3. The method of claim 2 further characterized by said vesicle having a shell wall membrane formed by said lipid component and said ganglioside component.

4. The method of claim 3 wherein said shell wall membrane contains a stabilizing component.

5. The method of claim 1 wherein said phospholipid component is selected from
   dipalmitoyl phosphatidylcholine;
   distearoyl phosphatidylcholine;
   dimyristyl phosphatidylcholine;
   dipalmitoyl phosphatidylethanolamine;
   distearoyl phosphatidylethanolamine
   dimyristyl phosphatidylethanolamine;
   dipalmitoyl phosphatidylserine;
   distearyol phosphatidylserine; and
   dimyristoyl phosphatidylserine 6. The method of claim 5 wherein said phospholipid component is selected from
   dipalmitoyl phosphatidylcholine;
   distearoyl phosphatidylcholine;
   dipalmitoyl phosphatidylserine; and
   distearoyl phosphatidylserine.

7. The method of claim 6 wherein said phospholipid component is dipalmitoyl phosphatidylcholine.

* * * * *